(12) United States Patent
Fujii

(10) Patent No.: US 10,188,285 B2
(45) Date of Patent: Jan. 29, 2019

(54) IMAGING APPARATUS

(71) Applicant: CANON KABUSHIKI KAISHA, Tokyo (JP)

(72) Inventor: Eiichi Fujii, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 78 days.

(21) Appl. No.: 15/319,347

(22) PCT Filed: Jun. 12, 2015

(86) PCT No.: PCT/JP2015/002953
§ 371 (c)(1),
(2) Date: Dec. 15, 2016

(87) PCT Pub. No.: WO2015/194145
PCT Pub. Date: Dec. 23, 2015

(65) Prior Publication Data
US 2017/0127937 A1    May 11, 2017

(30) Foreign Application Priority Data

Jun. 18, 2014 (JP) ................................. 2014-125735

(51) Int. Cl.
*A61B 3/14*        (2006.01)
*A61B 3/10*        (2006.01)
(Continued)

(52) U.S. Cl.
CPC ............ *A61B 3/102* (2013.01); *A61B 3/1225* (2013.01); *G01B 9/02004* (2013.01);
(Continued)

(58) Field of Classification Search
CPC ......... A61B 3/102; A61B 3/14; A61B 3/1225; A61B 3/12; A61B 3/1025; A61B 5/0066;
(Continued)

(56) References Cited

U.S. PATENT DOCUMENTS 7,468,997 B2 * 12/2008 Jayaraman ............ A61B 3/102
372/20
7,843,976 B2    11/2010 Cable

FOREIGN PATENT DOCUMENTS

JP    H05-327121 A    12/1993
JP    2008-122295 A    5/2008
(Continued)

OTHER PUBLICATIONS

Lu, et al., "Handheld ultrahigh speed swept source optical coherence tomography instrument using a MEMS scanning mirror", published Dec. 20, 2013, Biomedical Optics Express, Jan. 1, 2014, vol. 5, No. 1, Optical Society of America, USA.

Grulkowski, et al., "Retinal, anterior segment and full eye imaging using ultrahigh speed swept source OCT with vertical-cavity surface emitting lasers", published Oct. 3, 2012, Biomedical Optics Express, Nov. 1, 2012, vol. 3, No. 11, Optical Society of America, USA.

Klein, et al., "Multi-MHz retinal OCT", published Aug. 30, 2013, Biomedical Optics Express, Oct. 1, 2013, vol. 4, No. 10, Optical Society of America, USA.

*Primary Examiner* — Hung Dang
(74) *Attorney, Agent, or Firm* — Canon U.S.A., Inc. IP Division

(57) ABSTRACT

To acquire information on sections of an object with high accuracy even if the area to be imaged with a single scan is wide. A scanning unit is configured such that an angle of linear scanning of a fundus with illuminating light is 47 degrees or greater in the air. A light-source unit 10 includes a MEMS-VCSEL 601 whose coherence length during the sweeping of the frequency of the light is 14 or longer.

17 Claims, 6 Drawing Sheets

(51) Int. Cl.
*G01B 9/02* (2006.01)
*H01S 5/183* (2006.01)
*A61B 3/12* (2006.01)
*G02B 26/10* (2006.01)

(52) U.S. Cl.
CPC ....... *G01B 9/02091* (2013.01); *G02B 26/105* (2013.01); *G02B 26/106* (2013.01); *H01S 5/18366* (2013.01); *G01B 2290/65* (2013.01)

(58) Field of Classification Search
CPC ....... A61B 3/0008; A61B 3/13; A61B 1/0638; A61B 2090/3735; A61B 5/14555

USPC ................................. 351/206, 221, 246, 205
See application file for complete search history.

(56) References Cited

FOREIGN PATENT DOCUMENTS

| | | |
|---|---|---|
| JP | 2012-115578 A | 6/2012 |
| JP | 2012-213433 A | 11/2012 |
| JP | 2013-153882 A | 8/2013 |
| JP | 2013153884 A | 8/2013 |
| JP | 2014-144178 A | 8/2014 |
| JP | 2015-102537 A | 6/2015 |

* cited by examiner

[Fig. 1]
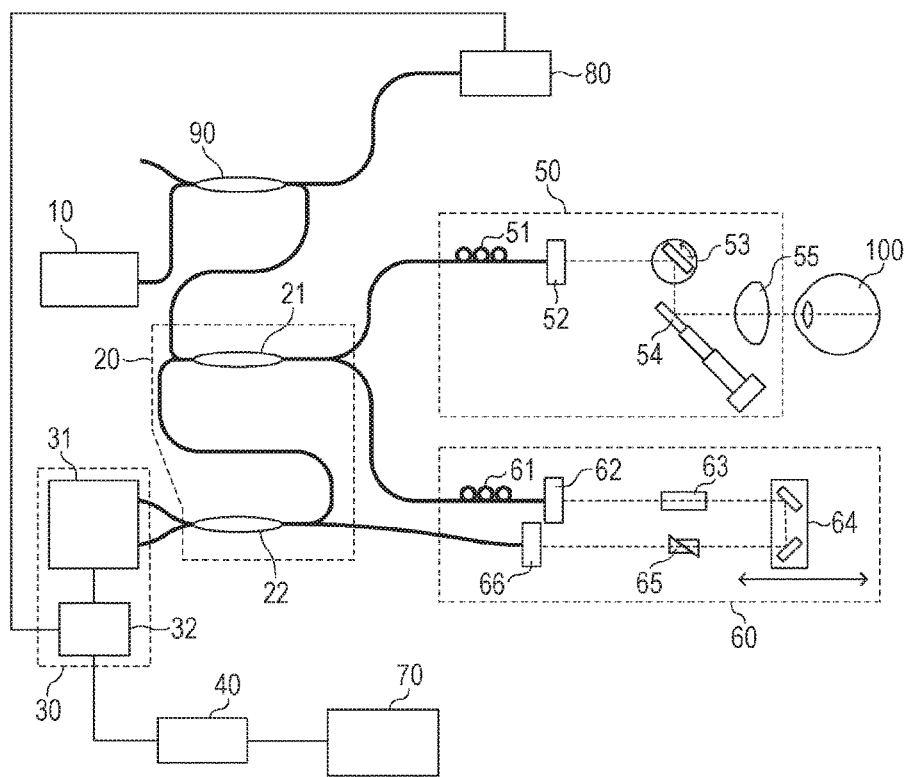

[Fig. 2A]
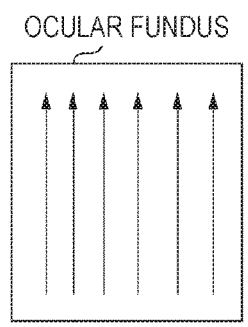
[Fig. 2B]
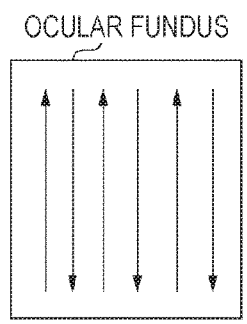
[Fig. 2C]
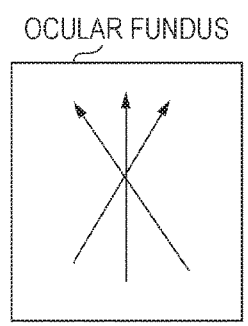
[Fig. 2D]
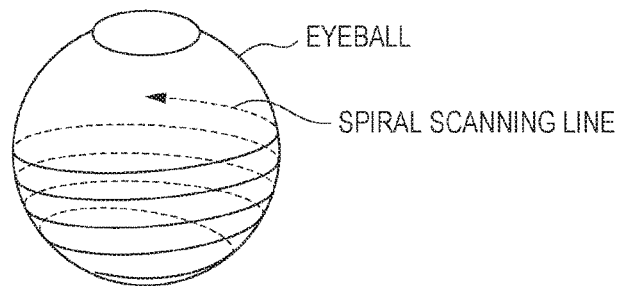

[Fig. 3]
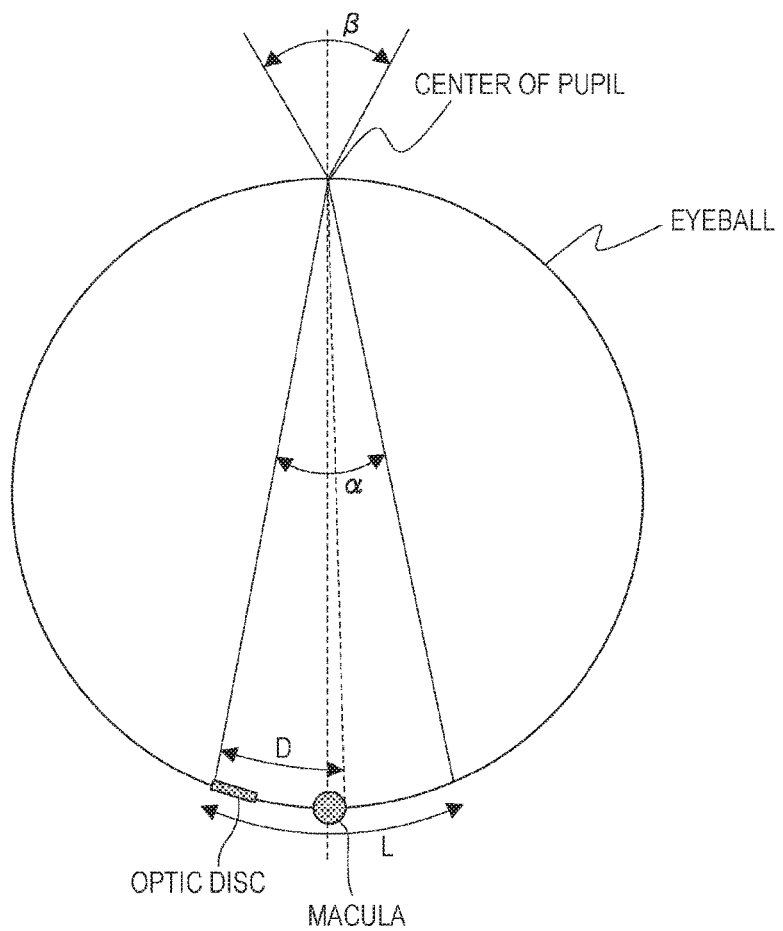

[Fig. 4]
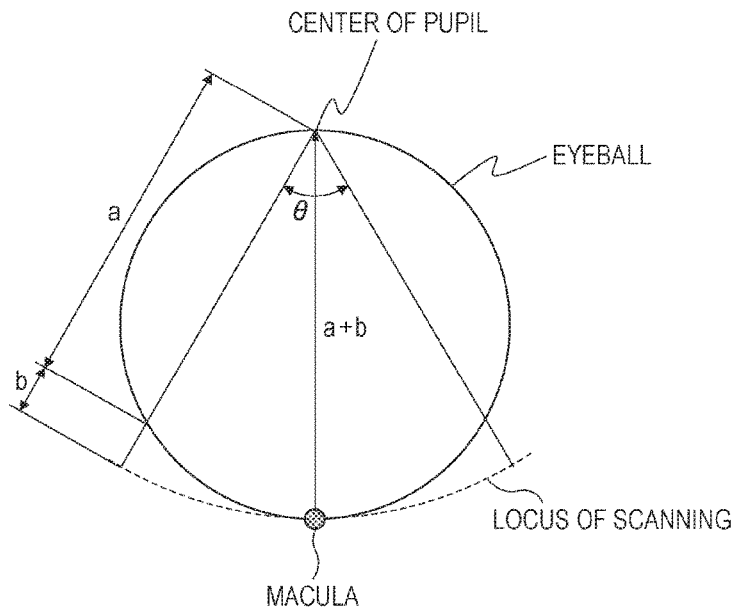
[Fig. 5]
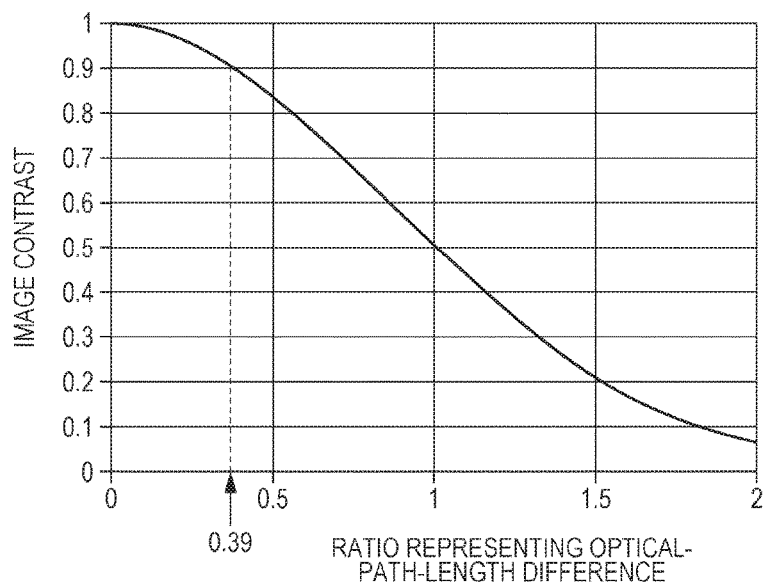

[Fig. 6]
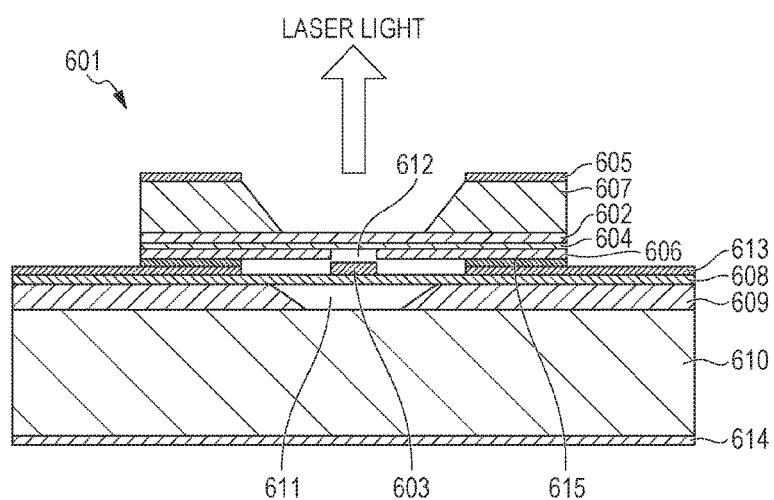

[Fig. 7]
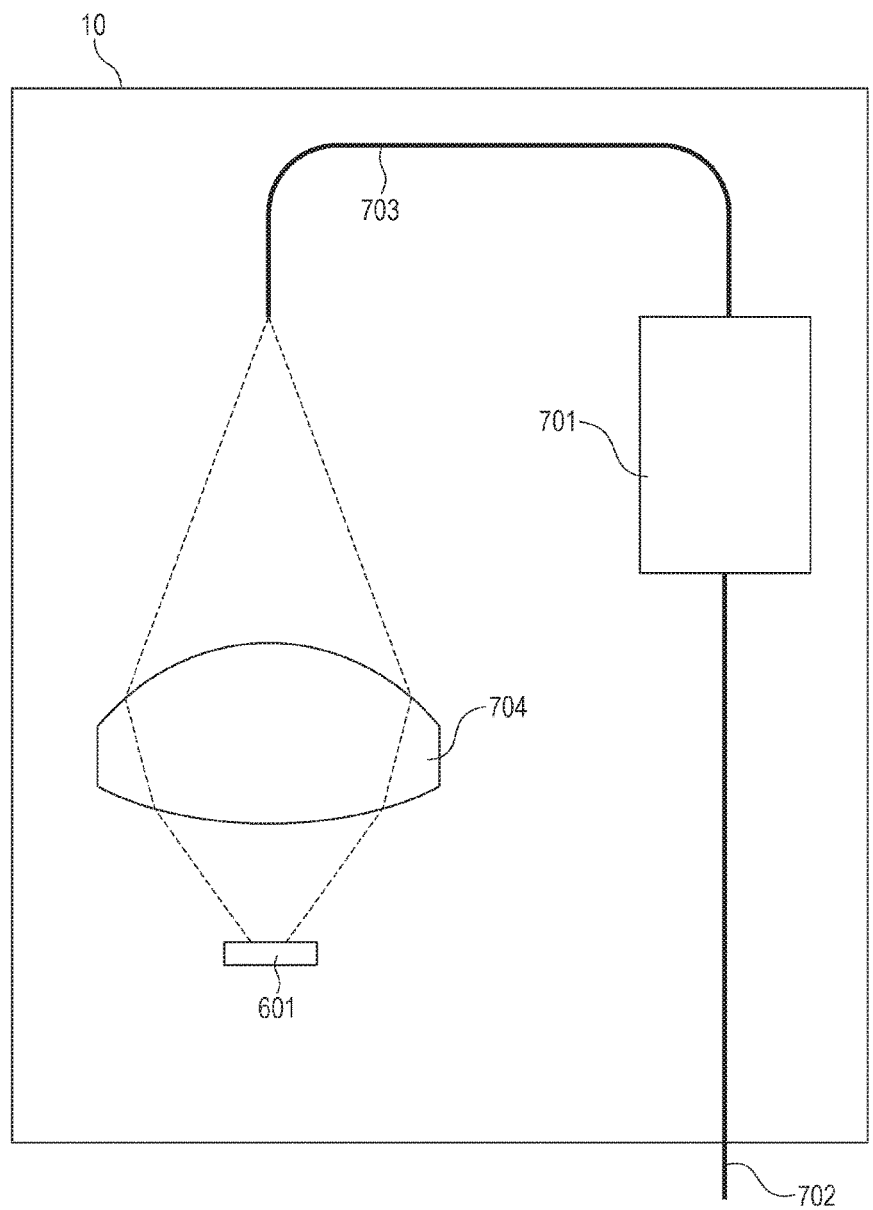

IMAGING APPARATUS

TECHNICAL FIELD

The present invention relates to an imaging apparatus configured to take an optical coherence tomographic image.

BACKGROUND ART

Imaging apparatuses employing optical coherence tomography (hereinafter abbreviated to OCT) have hitherto been developed (see PTL 1, an imaging apparatus employing OCT is hereinafter referred to as OCT apparatus). An OCT apparatus illuminates an object while changing the wavelength of the illuminating light, thereby causing reference light and each of reflections that are fed back from different depths of the object to interfere with each other, thereby generating interfering light. Then, frequency components of a temporal waveform representing the intensity of the interfering light are analyzed. Thus, information on a section of the object, specifically, a tomographic image, can be obtained. The OCT apparatus is used in, for example, an examination of an ocular fundus.

Many ocular diseases are difficult to completely cure. Therefore, it is important to find any lesions in the fundus in earlier stages and to start, in earlier stages, any treatment that slows down the spreading of such a lesion over a wide area of the fundus. Particularly, if the lesion reaches the macula, the eyesight is seriously affected. Hence, there is a demand for finding any lesions even if such lesions are still far away from the macula. To meet such a demand, the OCT apparatus used in fundus examinations is expected to have a wider angle of view.

According to PTL 1, to widen the area of the fundus that is observable as a tomographic image, a plurality of tomographic images are connected to one another, whereby a tomographic image of a wide area is obtained. The apparatus disclosed by PTL 1 is an OCT apparatus employing a wavelength-variable light source (a swept-source OCT apparatus). According to PTL 1, examples of the wavelength-variable light source include a fiber-ring resonator and a wavelength-selective filter.

CITATION LIST

Patent Literature

PTL 1: Japanese Patent Laid-Open No. 2012-115578

SUMMARY OF INVENTION

Technical Problem

The image-processing operation performed by the apparatus disclosed by PTL 1 for successively connecting the plurality of tomographic images acquired is time-consuming and troublesome. Therefore, information on sections in a wide area may be acquired with a single imaging action. In such a case, since the eyeball is substantially spherical, the optical-path length of the illuminating light significantly varies between a central portion and a peripheral portion of the fundus. In the case where the optical-path length of the illuminating light varies with the measurement position of the fundus, if the wavelength-variable light source according to PTL 1 having a short coherence length is used, the intensity of the resulting interference signal varies with the measurement position. Therefore, information on sections in a wide area cannot be acquired accurately.

In view of the above problems, the present invention provides an imaging apparatus that is capable of acquiring information on sections of an object with high accuracy even if the area to be imaged with a single scan is wide.

Solution to Problem

According to an aspect of the present invention, there is provided an imaging apparatus including a light-source unit configured to emit light while sweeping a frequency of the light; an interference unit configured to separate the light emitted from the light-source unit into illuminating light to be applied to a fundus and reference light, and to generate interfering light formed of reflected light, which is light applied to the fundus and reflected by the fundus, and the reference light; a scanning unit configured to scan the fundus with the illuminating light; a detecting unit configured to detect the interfering light; and an information-acquiring unit configured to acquire information on the fundus from the interfering light. The scanning unit is configured such that an angle of linear scanning of the fundus with the illuminating light is 47 degrees or greater in the air. The light-source unit includes a surface-emitting laser, the surface-emitting laser including a first reflector, a second reflector, and an active layer provided between the first reflector and the second reflector. When at least one of the first reflector and the second reflector is driven, a distance between the first reflector and the second reflector changes and the frequency of the light emitted changes. A coherence length of the surface-emitting laser during the sweeping of the frequency of the light is 14 mm or longer.

Advantageous Effects of Invention

According to the above aspect of the present invention, information on sections of an object can be acquired with high accuracy even if the area to be imaged with a single scan is wide.

Further features of the present invention will become apparent from the following exemplary embodiment with reference to the attached drawings.

BRIEF DESCRIPTION OF DRAWINGS

FIG. 1 is a schematic diagram of an exemplary OCT apparatus according to an embodiment of the present invention.

FIG. 2A is a schematic diagram of an exemplary method of scanning with illuminating light performed by a scanning unit included in the OCT apparatus according to the embodiment of the present invention.

FIG. 2B is a schematic diagram of another exemplary method of scanning with illuminating light performed by the scanning unit included in the OCT apparatus according to the embodiment of the present invention.

FIG. 2C is a schematic diagram of yet another exemplary method of scanning with illuminating light performed by the scanning unit included in the OCT apparatus according to the embodiment of the present invention.

FIG. 2D is a schematic diagram of yet another exemplary method of scanning with illuminating light performed by the scanning unit included in the OCT apparatus according to the embodiment of the present invention.

FIG. 3 is a schematic diagram of an eyeball.

FIG. 4 is a diagram illustrating a problem that arises with the increase in the angle of view.

FIG. 5 is a graph illustrating the coherence length.

FIG. 6 is a schematic diagram of an exemplary MEMS-VCSEL according to the embodiment of the present invention.

FIG. 7 is a schematic diagram of a light-source unit according to Example 1.

DESCRIPTION OF EMBODIMENT

An embodiment of the present invention will now be described. Note that the present invention is not limited to the following embodiment. FIG. 1 illustrates an exemplary configuration of an imaging apparatus (OCT apparatus) according to an embodiment of the present invention that employs optical coherence tomography. The OCT apparatus includes a light-source unit (light-source device) 10 that emits light while sweeping the frequency of the light, an interference unit (interference device) 20 that generates interfering light, a detecting unit (detecting device or detector) 30 that detects the interfering light, and an information-acquiring unit (information-acquiring device) 40 that acquires information on a fundus of an examination object 100 on the basis of the interfering light. The OCT apparatus further includes a measuring arm 50 and a reference arm 60.

The interference unit 20 includes couplers 21 and 22. The coupler 21 separates the light emitted from the light-source unit 10 into illuminating light to be applied to the fundus and reference light. The illuminating light is applied to the examination object 100 via the measuring arm 50. More specifically, the illuminating light that has entered the measuring arm 50 undergoes an adjustment of the state of polarization thereof that is performed by a polarization controller 51, and emerges as spatial light from a collimator 52. Subsequently, the illuminating light is applied to the fundus of the examination object 100 via an X-axis scanner 53, a Y-axis scanner 54, and a focus lens 55. The X-axis scanner 53 and the Y-axis scanner 54 are each a scanning unit (scanning device) having a function of scanning the fundus with the illuminating light. The position of the fundus that is to be illuminated with the illuminating light is changed by the scanning unit. Backscattered light (reflected light) from the fundus emerges from the measuring arm 50 via the focus lens 55, the Y-axis scanner 54, the X-axis scanner 53, the collimator 52, and the polarization controller 51, and enters the coupler 22 via the coupler 21.

On the other hand, the reference light travels through the reference arm 60 and enters the coupler 22. More specifically, the reference light that has entered the reference arm 60 undergoes an adjustment of the state of polarization thereof that is performed by a polarization controller 61, and emerges as spatial light from a collimator 62. Subsequently, the reference light travels through a dispersion-compensation glass 63, an optical-path-length-adjusting system 64, and a dispersion-adjusting prism pair 65, enters an optical fiber via a collimator lens 66, emerges from the reference arm 60, and enters the coupler 22.

The light backscattered (reflected) by the examination object 100 and traveled through the measuring arm 50 and the light traveled through the reference arm 60 interfere with each other in the coupler 22, whereby interfering light is generated. The interfering light is detected by the detecting unit 30. The detecting unit 30 includes a balanced detector 31 and an analog-digital (A/D) converter 32. In the detecting unit 30, immediately after the generation of interfering light in the coupler 22, the interfering light is demultiplexed and is detected by the balanced detector 31. The detected interfering light is converted into an electrical signal, i.e., an interference signal, by the balanced detector 31. The interference signal is converted into a digital signal by the A/D converter 32. The digital signal is transmitted to the information-acquiring unit 40, where the digital signal undergoes a frequency analysis such as Fourier transform, whereby information on the fundus is acquired. The information on the fundus thus acquired is displayed as a tomographic image on a display unit 70. The information-acquiring unit 40 can be provided with an information processing apparatus, such as a CPU. MPU or memory, and circuitry.

In the OCT apparatus illustrated in FIG. 1, the interfering light is sampled at regular optical-frequency intervals (at regular wave-number intervals) on the basis of a k-clock signal generated by a k-clock-generating unit 80 provided on the outside of the light-source unit 10. To extract and supply a portion of the light from the light-source unit 10 to the k-clock-generating unit 80, a coupler 90 is provided. The k-clock-generating unit 80 and the coupler 90 may be included in the light-source unit 10.

The above description concerns a process of acquiring information on a section taken at a single point of the examination object 100. Such a process of acquiring information on a section of the examination object 100 that is taken in the depth direction is referred to as A-scan. A process of acquiring information on a section of the examination object 100 that is taken in a direction orthogonal to the direction of A-scan, in other words, a process of scanning for acquiring a two-dimensional image, is referred to as B-scan. A process of scanning in a direction orthogonal to both the direction of A-scan and the direction of B-scan is referred to as C-scan. In two-dimensional raster scan performed along the surface of the fundus so as to acquire a three-dimensional tomographic image, high-speed scan corresponds to B-scan, and low-speed scan in which B-scan is performed repeatedly while the position of scanning is changed in a direction orthogonal to the B-scan direction corresponds to C-scan. Performing A-scan and B-scan provides a two-dimensional tomographic image. Performing A-scan, B-scan, and C-scan provides a three-dimensional tomographic image. B-scan and C-scan are performed by the X-axis scanner 53 and the Y-axis scanner 54, respectively.

The X-axis scanner 53 and the Y-axis scanner 54 include respective deflecting mirrors positioned such that the respective axes of rotation thereof are orthogonal to each other. The X-axis scanner 53 performs scanning in the X-axis direction. The Y-axis scanner 54 performs scanning in the Y-axis direction. The X-axis direction and the Y-axis direction are both perpendicular to the axial direction of the eyeball and are perpendicular to each other. The directions of line scans such as B-scan and C-scan do not each necessarily correspond to the X-axis direction or the Y-axis direction. Therefore, the directions of line scans such as B-scan and C-scan can be determined appropriately in accordance with the kind of a two-dimensional or three-dimensional tomographic image that is desired to be taken.

Moreover, various types of scans can be performed by simultaneously driving the X-axis scanner 53 and the Y-axis scanner 54 and changing the angles of the respective deflecting mirrors. For example, raster scan illustrated in FIG. 2A or 2B may be performed. For another example, as illustrated in FIG. 2C, a specific point (for example, the macula) of the eyeball may be scanned for a plurality of times. For yet another example, as illustrated in FIG. 2D, scan may be performed spirally with respect to a specific point (for example, the macula) of the eyeball.

In the field of fundus examinations, there is a demand for simultaneous imaging of the macula and the optic disc with a single scan. The area to be scanned (the angle of scanning) with the illuminating light of the OCT apparatus that meets the foregoing demand will now be described with reference to FIG. 3. FIG. 3 is a schematic diagram of an eyeball that is assumed to be a spherical body. The macula is at a position opposite to the center of the pupil of the eyeball. The optic disc is at a short distance from the macula. The macula and the optic disc are particularly important sites in the fundus.

In the fundus of a typical adult, a distance D between and inclusive of the macula and the optic disc is about 5.75 mm. The illuminating light is rotated about the center of the pupil of the eyeball, whereby the fundus is scanned. To take an image of an area centered on the macula and including the optic disc with a single scan, a length L of a curve (an imaging area) connecting the macula and the optic disc needs to be at least about 14 mm, considering individual differences. Here, the angle of deflection of the illuminating light that is rotated about the center of the pupil so as to define the imaging area having the above length L is denoted by $\alpha$. The average diameter of the adult eyeball is about 24 mm. Therefore, to set the length L of the imaging area to 14 mm or larger, the angle of deflection $\alpha$ needs to be set to 33.4 degrees or greater. Since the average refractive index in the eyeball is 1.38, the angle of deflection $\alpha$ corresponds to an in-the-air angle of deflection $\beta$ of the illuminating light that is incident on the center of the pupil. The in-the-air angle of deflection $\beta$ is expressed as $\arcsin(1.38 \times \sin(33.4 \text{ degrees}/2)) \times 2$, which is approximately equal to 47 degrees. That is, to image the macula and the optic disc simultaneously with the macula being the center of the imaging area, the in-the-air angular range of linear scanning of the fundus with the illuminating light is set to 47 degrees or greater. Hereinafter, the in-the-air angular range of linear scanning of the fundus with the illuminating light is defined as the angle of view. That is, the angle of deflection $\beta$ is defined as the angle of view.

Now, a problem that arises in the scanning at the angle of deflection $\beta$ will be described with reference to FIG. 4. FIG. 4 is a schematic diagram of an eyeball that is assumed to be a spherical body, as in FIG. 3. The broken line illustrated in FIG. 4 represents the locus of scanning. As illustrated in FIG. 4, the physical distance from the center of the pupil to the outer wall, i.e., the fundus, of the eyeball is a+b at the macula but is a at a certain distance (defined by an angle of $\theta/2$) from the macula. On the basis of an axial length T of the eye and an angle of deflection $\theta$ in the eyeball, a and b are expressed as follows:

$$a = T \times \cos(\theta/2) \quad \text{Expression 1}$$

$$a + b = T \quad \text{Expression 2}$$

The difference between the distance from the center of the pupil to the macula and the distance from the center of the pupil to the position at a certain distance from the macula is b. The difference b increases with the angle $\theta$. Therefore, in an OCT apparatus intended for fundus examinations and having a wide angle of view, the difference between the optical-path length from the center of the pupil to the macula and the distance from the center of the pupil to a peripheral position at a certain distance from the macula is large. The axial length T of an adult eye varies greatly with individuals, and the eyes of 95% of the adults each have an axial length T of 21 mm or longer and 28 mm or shorter. Herein, the maximum value of 28 mm among the foregoing range is taken as the axial length T of the eye. If the angle of deflection $\theta$ in the eyeball is 33.4 degrees, b is about 1.2 mm, according to Expressions 1 and 2.

Tissue of the fundus observed by the OCT apparatus intended for fundus examinations include the retina near the surface of the fundus, and the choroid behind the retina. The retina has a maximum thickness of about 0.50 mm. The choroid has a maximum thickness of about 0.30 mm. Therefore, the OCT apparatus intended for fundus examinations needs to be capable of imaging to a depth of at least 0.80 mm. That is, there is a difference of 0.8 mm between the distance from the center of the pupil to the surface of the fundus and the distance from the center of the pupil to the choroid.

Hence, to image the macula and the optic disc simultaneously with a single scan and to acquire information on a region near the surface of the optic disc and information on the choroid behind the macula with substantially the same accuracy, the light source needs to have such coherency that a satisfactory interference signal is obtained even if the difference between the above distances is 2×(b+0.80), which is approximately equal to 4.0 mm. The difference between the distances corresponds to an in-the-air optical-path-length difference of 4.0 mm×1.38, which is approximately equal to 5.5 mm. That is, to provide an OCT apparatus that is capable of acquiring accurate information on sections of an object with angle of view of 47 degrees or greater, the OCT apparatus needs to include a light source that enables the acquisition of an interference signal having a satisfactory intensity even if there is an in-the-air optical-path-length difference of 5.5 mm.

To acquire an interference signal even if there is an optical-path-length difference of 5.5 mm, a light source having a coherence length of 5.5 mm or longer may be used, in general. In an OCT apparatus for medical use, however, such a coherence length is insufficient. This is because, if there is an optical-path-length difference that is equal to the coherence length, the intensity of the interference signal is reduced to half the intensity of the interference signal obtained when there is no optical-path-length difference.

In medical imaging, to increase the accuracy in image interpretation, the brightness and the contrast of the image need to be controlled with high accuracy. In "Quality Assurance (QA) Guideline for Medical Imaging Display Systems" issued by Japan Medical Imaging and Radiological Systems Industries Association, it is specified that, if image interpretation is conducted by using multiple monitors, the difference in brightness between the monitors needs to be 10% or smaller. That is, the difference in brightness between different positions in a single image under the 100% luminosity is desirably 10% or smaller. To satisfy this condition, the OCT apparatus may be configured such that the roll-off characteristic of the interference signal in the case where there is an optical-path-length difference of 5.5 mm is −10% or smaller.

In many optical-frequency-swept light sources, the instantaneous spectrum has a substantially Gaussian shape. Therefore, the interference signal with respect to the optical-path-length difference rolls off along a substantially Gaussian curve. FIG. 5 is a graph illustrating the roll-off characteristic of image contrast, corresponding to the intensity of the interference signal, with respect to the optical-path-length difference. The optical-path-length difference represented by the horizontal axis is normalized to one at a value of image contrast that is half the value of image contrast obtained when there is no optical-path-length difference. The optical-path-length difference at a value of image contrast that is half the value of image contrast obtained when there is no optical-path-length difference is referred to as coherence length. The image contrast may be regarded as the intensity of the interference signal or the brightness.

Referring to FIG. 5, when the roll-off characteristic is Gaussian, the optical-path-length difference that reduces the peak of image contrast (obtained when there is no optical-path-length difference) by 10% is 0.39 times the coherence length at which the peak of image contrast is reduced by half. Hence, to satisfy the above condition, the coherence length needs to be at least 5.5 mm/0.39, which is approximately equal to 14 mm. That is, the coherence length of an optical-frequency-swept light source needs to be 14 mm or longer during the sweeping of the optical frequency.

If the fundus is imaged with a wide angle of view, the number of imaging points for obtaining a tomographic image needs to be increased because the angle of view is wide. To increase the number of imaging points, A-scan needs to be performed at a high speed. To perform A-scan at a high speed, the sweep frequency of the light source needs to be 200 kHz or higher. That is, an OCT apparatus having an angle of view of 47 degrees or greater as described above needs to include a light source that is capable of sweeping the optical frequency at a high speed and has a long coherence length. In this respect, it is most suitable to control the oscillation wavelength of a vertical-cavity surface-emitting laser (hereinafter abbreviated to VCSEL) by using a microelectromechanical-systems (hereinafter abbreviated to MEMS) technology. That is, a so-called MEMS-VCSEL is the most suitable light source. Hence, the OCT apparatus according to the embodiment of the present invention whose angle of view is 47 degrees or greater includes an optical-frequency-swept light source including a MEMS-VCSEL whose coherence length is 14 mm or longer. The OCT apparatus having such a configuration exhibits high performance in the diagnosis of ocular diseases and having a high clinical value. The term "MEMS-VCSEL" refers to a VCSEL including a movable reflector that is lithographically fabricated by a micromachining technique such as sacrificial-layer etching.

FIG. 6 is a schematic sectional view of an exemplary MEMS-VCSEL 601. The MEMS-VCSEL 601 includes a first reflector 602, a second reflector 603, and an active layer 604 provided between the first reflector 602 and the second reflector 603. An electrical charge is injected into the active layer 604 from a first electrode 605 and from a second electrode 606, whereby the active layer 604 emits light. Therefore, the active layer 604 is provided between the first electrode 605 and the second electrode 606. The first electrode 605 is provided across a substrate 607 from the active layer 604.

The second reflector 603 is provided on a movable beam 608 and at a position corresponding to at least a light-emitting area. The second reflector 603 is driven via the movable beam 608. The movable beam 608 is supported by a substrate 610 with a gap-producing layer 609 interposed therebetween. The gap-producing layer 609 has a gap 611. The gap 611 allows a portion of the movable beam 608 where the second reflector 603 is provided to move in the thickness direction. Likewise, another gap 612 is provided between the second reflector 603 and the active layer 604.

The movable beam 608 is an electrically conductive member. When a voltage is applied between a third electrode 613, which is electrically connected to the movable beam 608, and a fourth electrode 614, which is provided across the substrate 610 from the third electrode 613, an electrostatic force is generated, whereby the movable beam 608 and the second reflector 603 are driven together. Consequently, the portion of the movable beam 608 where the second reflector 603 is provided moves in the thickness direction, and the distance between the first reflector 602 and the second reflector 603 changes. In accordance with the changed distance, the wavelength is intensified. Consequently, the oscillation wavelength (optical frequency) of light emitted from the MEMS-VCSEL 601 changes.

In the MEMS-VCSEL 601 illustrated in FIG. 6, the second reflector 603 provided opposite the light-emitting side with respect to the active layer 604 is driven. Alternatively, the first reflector 602 provided on the light-emitting side with respect to the active layer 604 may be driven. Moreover, both the first reflector 602 and the second reflector 603 may be driven.

The MEMS-VCSEL 601 is manufactured as follows. The substrate 607 provided with the first reflector 602, the active layer 604, the first electrode 605, and the second electrode 606 is bonded, with a bonding layer 615, to the substrate 610 provided with the second reflector 603, the movable beam 608, the gap-producing layer 609, the third electrode 613, and the fourth electrode 614. The substrate 607 provided on the light-emitting side has an opening in a portion thereof corresponding to the light-emitting area so as to suppress the absorption of laser light.

Materials for the active layer 604, the substrate 607, the first reflector 602, and other elements may be selected in accordance with the wavelength used in the OCT apparatus. Exemplary materials include GaAs-based materials. One of major components of the eyeball and other kinds of tissue is water. To suppress the absorption of laser light by water, the center wavelength of the oscillation wavelength may be set to 1040 nm or longer and 1080 nm or shorter (277.6 GHz or higher and 288.3 GHz or lower). The oscillation wavelength band may be set to a range of +/−30 nm or more with respect to the center wavelength.

The first reflector 602 and the second reflector 603 may each be a multilayer film. More specifically, the first reflector 602 and the second reflector 603 may each be a distributed Bragg reflector (hereinafter abbreviated to DBR). The DBR includes high-refractive-index layers each having a relatively high refractive index and low-refractive-index layers each having a relatively low refractive index. The high-refractive-index layers and the low-refractive-index layers are stacked alternately. The high-refractive-index layers and the low-refractive-index layers differ in elements thereof or, even if the elements thereof are the same, in the composition ratio of the elements. The optical thicknesses of the high-refractive-index layers and the low-refractive-index layers may each be set to an odd-number multiple of $\lambda/4$, where $\lambda$ denotes the center wavelength. The DBR may be made of a semiconductor multilayer film or a dielectric multilayer film.

The first reflector 602 and the second reflector 603 are each not necessarily a DBR. For example, the first reflector 602 and the second reflector 603 may each be a diffraction grating, more specifically, a high-refractive-index-difference subwavelength-diffraction-grating (high-index-contrast grating, hereinafter abbreviated to HCG) mirror. The HCG mirror includes high-refractive-index portions and low-refractive-index portions are arranged alternately and periodically in the in-plane direction. For example, portions of a high-refractive-index member (made of, for example. $Al_{0.7}Ga_{0.3}As$) are removed, whereby slits (open portions) are provided periodically, which provides a configuration in which high-refractive-index areas (made of $Al_{0.7}Ga_{0.3}As$) and low-refractive-index areas (made of the air) are arranged alternately and periodically in the in-plane direction. The HCG mirror can have a one-dimensional or two-dimensional periodic structure. If such an HCG mirror is used as the second reflector 603, the movable beam 608 and the second reflector 603 are desirably combined into an integral body.

One of the first reflector 602 and the second reflector 603 that is on the light-emitting side (in the configuration illustrated in FIG. 6, the first reflector 602) may have a reflectance of 99.0% or higher and 99.7% or lower. The other reflector (in the configuration illustrated in FIG. 6, the second reflector 603) provided on a side opposite the light-emitting side may have a reflectance of 99.5% or higher. These reflectance values apply to all wavelengths in the oscillation wavelength band.

The coherence length of the MEMS-VCSEL 601 during the sweeping of the optical frequency can be increased by increasing the reflectances of the first reflector 602 and the second reflector 603. If the reflectances are within the respective ranges described above, the coherence length of the MEMS-VCSEL 601 during the sweeping of the optical frequency can be set to 14 mm or longer. To further increase the coherence length, the reflectance of the second reflector 603, which is to be driven, may be made as high as possible. In contrast, if the reflectance of the first reflector 602 provided between the active layer 604 and the first electrode 605 for injecting an electrical charge into the active layer 604 is increased, the coherence length increases, whereas the optical output power is lowered as a trade-off. Therefore, the reflectance of the first reflector 602 is set to an appropriate value within the above range. To set the coherence length during the sweeping of the optical frequency to 23 mm or longer, the reflectance of the first reflector 602, which is on the light-emitting side, may be set to 99.3% or higher and 99.7% or lower.

The active layer 604 may have a gain in a wide wavelength band. Specifically, the active layer 604 may have a satisfactory gain in a wavelength band that is wider than the wavelength band of reflections from the first reflector 602 and the second reflector 603. For example, the active layer 604 may have a quantum-well structure that is capable of emitting light at two or more different energy levels. The quantum-well structure may be either a single quantum-well structure or a multiple quantum-well structure. In the case of a multiple quantum-well structure, the active layer 604 may include a plurality of quantum wells in which well potentials all have the same depth and wells all have the same width, or in which well potentials have different depths and wells have different widths.

The above description concerns an exemplary method of exciting the active layer 604 in which an electrical charge is injected into the active layer 604 from the first electrode 605 and the second electrode 606. For another example, photo-excitation may be performed by using an external light source. In the latter case, the first electrode 605 and the second electrode 606 are not necessary.

To increase the speed of sweeping of the optical frequency, the frequency of the alternating voltage to be applied to the third electrode 613 and the fourth electrode 614 may be increased. Furthermore, the frequency of resonance between the respective materials forming the second reflector 603 and the movable beam 608 may be increased so that the frequency of resonance becomes the same as the frequency of the alternating voltage. Thus, the second reflector 603 can undergo a high-speed and large displacement. Consequently, the MEMS-VCSEL 601 can operate at a high sweep speed and with a wide oscillation wavelength band. To increase the frequency of resonance between the materials forming the second reflector 603 and the movable beam 608, for example, the mass of one of or both of the second reflector 603 and the movable beam 608 may be reduced.

Recent-year demands include a demand for the observation of drusen in a peripheral portion of the fundus by using an OCT apparatus in the diagnosis of fundus diseases. Specifically, there has been a demand for an OCT apparatus that allows observation of a wide area defined by a length L of the imaging area (see FIG. 3) of 20 mm or greater. Setting the length L of the imaging area to 20 mm or greater means setting the angle of view to 68 degrees or greater. If the length L of the imaging area is 20 mm, b in Expression 2 representing the difference between the distance from the center of the pupil to the center of the fundus and the distance from the center of the pupil to the peripheral portion of the fundus is about 2.4 mm. The sum of the difference b and a depth of 0.8 mm is about 3.2 mm, which corresponds to an in-the-air optical-path-length difference of about 8.8 mm (=3.2×2×1.38). To acquire accurate information on a section even if there is such an optical-path-length difference, the coherence length of the light source during the sweeping of the optical frequency needs to be 23 mm or longer, considering the above roll-off characteristic.

As such a light source, the MEMS-VCSEL 601 described above can be employed. However, to increase the coherence length, the reflectances of the reflectors need to be increased. Consequently, the optical output of the MEMS-VCSEL 601 is reduced. Hence, the light-source unit 10 may include not only the MEMS-VCSEL 601 but also an optical amplifier that amplifies the optical output of the MEMS-VCSEL 601. An exemplary optical amplifier is a semiconductor optical amplifier.

An OCT apparatus whose angle of view is 68 degrees or greater is also desired to sweep the optical frequency at a rate of 400 kHz or higher, depending on the interval of imaging. Therefore, it is desirable to reduce the mass of the movable beam 608 and to increase the resonance frequency. Specifically, an HCG mirror including the second reflector 603 and the movable beam 608 that are provided as an integral body may be employed as the second reflector 603.

EXAMPLES

Examples of the present invention will now be described.

Example 1

In Example 1, the MEMS-VCSEL 601 illustrated in FIG. 6 is used as the optical-frequency-swept light source included in the light-source unit 10 of the OCT apparatus illustrated in FIG. 1. FIG. 7 illustrates details of the light-source unit 10. Since the optical output of the MEMS-VCSEL 601 is insufficient, the light-source unit 10 includes an optical amplifier 701, thereby amplifying the optical output of the MEMS-VCSEL 601. Specifically, the light-source unit 10 is configured such that an optical output of 20 mW is outputted from an output fiber 702. The light-source unit 10 further includes a lens 704 that focuses the light from the MEMS-VCSEL 601 on an optical fiber 703 that guides the light to the optical amplifier 701.

The light-source unit 10 emits light while sweeping the frequency of the light from a high level of 296.8 THz (1010 nm) to a low level of 270.1 THz (1110 nm). By sweeping the optical frequency from a high level to a low level, slightly higher optical output is obtained than in a case where the optical frequency is swept in the opposite way from a low level to a high level. Consequently, the quality of the resulting image is improved. The MEMS-VCSEL 601 may have a coherence length of 14 mm or longer during the sweeping of the optical frequency. In Example 1, the MEMS-VCSEL 601 has a coherence length of 20 mm.

Referring to FIG. 1, an operation of the OCT apparatus according to Example 1 will now be described. Light outputted from the light-source unit 10 is inputted to the coupler 90, which separates the light into two portions and transmits one of the portions of the light to the k-clock-generating unit 80. The ratio of separation by the coupler 90 is 0.95 to 0.05, which means 5% of the total quantity of light is transmitted to the k-clock-generating unit 80. The k-clock-generating unit 80 generates, from the light inputted thereto, a clock signal that pulsates at regular optical-frequency intervals. The k-clock-generating unit 80 is configured to generate a k-clock signal that pulsates at an optical-frequency interval of 10.6 GHz, which is necessary for imaging an area defined by an angle of view of 47 degrees and a depth (an intraocular depth) of 2.0 mm while the roll-off of the interference signal is suppressed to −10% or smaller. Specifically, the k-clock-generating unit 80 is a Mach-Zehnder interferometer.

The other portion of the light emitted from the coupler 90 enters the coupler 21 of the interference unit 20. The coupler 21 separates the light emitted from the light-source unit 10 into illuminating light to be applied to the fundus and reference light. The ratio of separation of the light by the coupler 21 is 3 to be introduced into the measuring arm 50 and 7 to be introduced into the reference arm 60. The illuminating light that has entered the measuring arm 50 undergoes an adjustment of the state of polarization thereof that is performed by the polarization controller 51, and emerges as spatial light from the collimator 52. Subsequently, the illuminating light is applied to the fundus of the examination object 100 via the X-axis scanner 53, the Y-axis scanner 54, and the focus lens 55, and is moved in such a manner as to linearly scan the fundus. The X-axis direction corresponds to a direction parallel to the line connecting the optic disc and the macula. The Y-axis direction is perpendicular to the X-axis direction. The area to be scanned by the X-axis scanner 53 and the area to be scanned by the Y-axis scanner 54 are each defined by an angle of view of 47 degrees. The X-axis scanner 53 and the Y-axis scanner 54 are each configured to scan an area centered on the macula. Backscattered light from the fundus of the examination object 100 is introduced into the optical fiber via the focus lens 55, the Y-axis scanner 54, the X-axis scanner 53, the collimator 52, and the polarization controller 51, and enters the coupler 22 via the coupler 21.

The reference light that has entered the reference arm 60 undergoes an adjustment of the state of polarization thereof that is performed by the polarization controller 61, and emerges as spatial light from the collimator 62. Subsequently, the reference light travels through the dispersion-compensation glass 63, the optical-path-length-adjusting system 64, and the dispersion-adjusting prism pair 65, enters the optical fiber via the collimator lens 66, and enters the coupler 22.

The backscattered light from the examination object 100 that has traveled through the measuring arm 50 and the light traveled through the reference arm 60 interfere with each other in the coupler 22, which generates interfering light. The interfering light is detected by the balanced detector 31 of the detecting unit 30. The interfering light is converted into an electrical signal, i.e., an interference signal, by the balanced detector 31. The interference signal is sampled by the A/D converter 32 synchronously with the k-clock generated by the k-clock-generating unit 80, and is thus converted into a digital signal that pulsates at regular optical-frequency intervals. The digital signal pulsating at regular optical-frequency intervals that has been acquired by the A/D converter 32 undergoes signal processing operations such as noise reduction, Fourier transform, and conversion into a tomographic image performed by the information-acquiring unit 40, whereby information on the fundus is acquired. The acquired information on the fundus is displayed as an image on the display unit 70.

The sweep frequency of the light-source unit 10 is set to 200 kHz, and tomographic images are taken at an interval of 20 μm in the X-axis direction and at an interval of 50 μm in the Y-axis direction. The number of images to be sampled is 196000. Thus, a tomographic image of the fundus in an area defined by an angle of view of 47 degrees, i.e., an area of size 14 mm by 14 mm, is taken in a little less than one second. The reason for setting the imaging interval in the X-axis direction to 20 μm is that the resolution of the OCT apparatus in the horizontal direction, which is restricted by the diameter of the pupil, is typically 20 μm, which is applied to Example 1. Meanwhile, to reduce the imaging time, the scanning interval in the Y-axis direction is increased to 50 μm, as in the known OCT apparatus.

Example 2

Example 2 differs from Example 1 in that the imaging interval in the X-axis direction is 20 μm and in that the sweep frequency is set to 245 kHz. In such a configuration, since the interval at which tomographic images are taken is 20 μm in each of the X-axis and Y-axis directions, it is possible to generate a tomographic image at any position in a processing operation performed thereafter. Hence, an OCT apparatus that allows free image interpretation is provided. Since the sweep frequency is set to 245 kHz, a tomographic image of an area of size 14 mm by 14 mm can be taken in two seconds. A typical patient can fix the eye for about two seconds at most. Since a single tomographic image can be acquired in two seconds or less, a good-quality image with few motion artifacts is acquired.

In Table 1. Examples 1 and 2 described above and Examples 3 and 4 to be described below are compared

TABLE 1

|  | Example 1 | Example 2 | Example 3 | Example 4 |
|---|---|---|---|---|
| Coherence length (mm) | 20 | 20 | 40 | 40 |
| Sweep frequency (kHz) | 200 | 245 | 400 | 500 |
| Angle of view (degrees) | 47 | 47 | 68 | 68 |
| Imaging area (mm by mm) | 14 by 14 | 14 by 14 | 20 by 20 | 20 by 20 |
| Imaging interval in X direction (μm) | 20 | 20 | 10 | 20 |
| Imaging interval in Y direction (μm) | 50 | 20 | 50 | 20 |

Example 3

As summarized in Table 1, Example 3 differs from Example 1 in the coherence length, the sweep frequency, the angle of view, the imaging area, the imaging interval in the X-axis direction, and the imaging interval in the Y-axis direction of the MEMS-VCSEL 601. Specifically, the angle of view is set to 68 degrees by increasing the angles of scanning by the X-axis scanner 53 and the Y-axis scanner 54. Consequently, in Example 3, an OCT apparatus capable of imaging an area of the fundus of 20 mm by 20 mm is provided, allowing the observation of drusen in a peripheral portion of the fundus. In Example 3, a MEMS-VCSEL 601 having a coherence length of 40 mm is used. The configuration of the MEMS-VCSEL 601 is substantially the same as that illustrated in FIG. 6, except the following. The reflectance of the first reflector 602 provided on the light-emitting side is higher than in Example 1, whereby the finesse is made higher than in Example 1. In addition, an HCG mirror in which the second reflector 603 and the movable beam 608 are combined into an integral body is employed as the second reflector 603. However, since the reflectance of the first reflector 602 is increased, the MEMS-VCSEL 601 according to Example 3 has a lower optical output than the MEMS-VCSEL 601 according to Example 1. Specifically, the optical output of the light-source unit 10 according to Example 3 is 10 mW.

Furthermore, to acquire a tomographic image of a 20 mm-by-20 mm area of the fundus in two seconds by taking images of sections in that area at an interval of 10 μm in the X-axis direction and at an interval of 50 μm in the Y-axis direction, the sweep frequency of the light-source unit 10 is set to 400 kHz.

Thus, Example 3 provides an OCT apparatus having a wide angle of view and allowing observation of drusen in a peripheral portion of the fundus with a single scan.

Example 4

As summarized in Table 1, Example 4 differs from Example 3 in the sweep frequency, the imaging interval in the X direction, and the imaging interval in the Y direction. Specifically, images of sections are taken at an interval of 20 μm in the X-axis direction and at an interval of 20 μm in the Y-axis direction. Furthermore, the sweep frequency is set to 500 kHz. Thus, a tomographic image of a 20 mm-by-20 mm area scanned at an interval of 20 μm is acquired in two seconds.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-125735, filed Jun. 18, 2014, which is hereby incorporated by reference herein in its entirety.

REFERENCE SIGNS LIST

10 Light-source unit
20 Interference unit
30 Detecting unit
40 Information-acquiring unit
53 X-axis scanner
54 Y-axis scanner

The invention claimed is:
1. An imaging apparatus comprising:
a light-source unit configured to emit light while sweeping a frequency of the light;
an interference unit configured to separate the light emitted from the light-source unit into illuminating light to be applied to a fundus and reference light, and to generate interfering light formed of reflected light, which is light applied to the fundus and reflected by the fundus, and the reference light;
a scanning unit configured to scan the fundus with the illuminating light;
a detecting unit configured to detect the interfering light; and
an information-acquiring unit configured to acquire information on the fundus from the interfering light,
wherein the scanning unit is configured such that an angle of linear scanning of the fundus with the illuminating light is 68 degrees or greater in the air,
wherein the light-source unit in hides a surface-emitting laser, the surface-emitting laser including a first reflector, a second reflector, and an active layer provided between the first reflector and the second reflector,
wherein, when at least one of the first reflector and the second reflector is driven, a distance between the first reflector and the second reflector changes and the frequency of the light emitted changes,
wherein a coherence length of the surface-emitting laser during the sweeping of the frequency of the light is 23 mm or longer, and
wherein a range of a depth of a tomographic image of the fundus to be obtained using the information on the fundus is 3.2 mm or more.

2. The imaging apparatus according to claim 1, wherein the frequency of the light emitted from the surface-emitting laser is swept at a rate of 200 kHz or higher.

3. The imaging apparatus according to claim 1, wherein the frequency of the light emitted from the surface-emitting laser is swept at a rate of 400 kHz or higher.

4. The imaging apparatus according to claim 1,
wherein the scanning unit includes a deflecting mirror, and
wherein the scanning unit scans the fundus with the illuminating light while changing an angle of the deflecting mirror.

5. The imaging apparatus according to claim 1, wherein the at least one of the first reflector and the second reflector that is driven has a diffraction grating.

6. The imaging apparatus according to claim 5, wherein the diffraction grating includes high-refractive-index portions and open portions that are arranged periodically.

7. The imaging apparatus according claim 1, wherein one of the first reflector and the second reflector that is on a light-emitting side has a reflectance of 99.0% or higher and 99.7% or lower.

8. The imaging apparatus according to claim 1, wherein one of the first reflector and the second reflector that is on a light-emitting side has a reflectance of 99.3% or higher and 99.7% or lower.

9. The imaging apparatus according to claim 1, wherein one of the first reflector and the second reflector that is on a side opposite a light-emitting side has a reflectance of 99.5% or higher.

10. The imaging apparatus according to claim 1, wherein the light-source unit further includes an optical amplifier configured to amplify the light emitted from the surface-emitting laser.

11. The imaging apparatus according to claim 1, further comprising a clock generation unit configured to include an interferometer having an optical path length difference and configured to generate a clock corresponding to the optical path length difference; and
an AD convertor configured to convert, by sampling the detected interfering light using the clock, the detected interfering light to a digital signal.

12. The imaging apparatus according to claim 1, further comprising a control unit configured to perform repeatedly the sweeping and the scanning of the scanning unit,
wherein the detecting unit detects the interfering light while the control unit is performing repeatedly.

13. An imaging apparatus comprising:
a light-source unit configured to emit light while sweeping a frequency of the light;
an interference unit configured to separate the light emitted from the light-source unit into illuminating light to be applied to a fundus and reference light, and to generate interfering light formed of reflected light, which is light applied to the fundus and reflected by the fundus, and the reference light;
a scanning unit configured to scan the fundus with the illuminating light;
a detecting unit configured to detect the interfering light; and
an information-acquiring unit configured to acquire information on the fundus from the interfering light,
wherein the scanning unit is configured such that an angle of linear scanning of the fundus with the illuminating light is 68 degrees or greater in the air,
wherein a coherence length of light-source unit during the sweeping of the frequency of the light is 23 mm or longer, and
wherein a range of a depth of a tomographic image of the fundus to be obtained using the information on the fundus is 3.2 mm or more.

14. The imaging apparatus according to claim 13, further comprising a clock generation unit configured to include an interferometer having an optical path length difference and configured to generate a clock corresponding to the optical path length difference; and
an AD convertor configured to convert, by sampling the detected interfering light using the clock, the detected interfering light to a digital signal.

15. The imaging apparatus according claim 14,
wherein the clock generation unit generates a clock at regular optical-frequency intervals, and
wherein the A/D converter convers the detected interfering light into digital data at the regular optical-frequency intervals.

16. The imaging apparatus according to claim 13, further comprising a control unit configured to perform repeatedly the sweeping and the scanning of the scanning unit,
wherein the detecting unit detects the interfering light while the control unit is performing repeatedly.

17. The imaging apparatus according to claim 13, wherein the tomographic image of the fundus to be obtained using the information on the fundus includes an imaging range of 20 mm or more in a direction intersecting a direction of the depth of the fundus.

* * * * *